United States Patent
Castañeda

(10) Patent No.: US 6,602,267 B2
(45) Date of Patent: Aug. 5, 2003

(54) ARTICULABLE AND RECIPROCABLE SURGICAL KNIFE

(75) Inventor: Javier E. Castañeda, Miami, FL (US)

(73) Assignee: Medcanica, Inc., Miami, FL (US)

( * ) Notice: Subject to any disclaimer, the term of this patent is extended or adjusted under 35 U.S.C. 154(b) by 0 days.

(21) Appl. No.: 09/981,862

(22) Filed: Oct. 17, 2001

(65) Prior Publication Data

US 2003/0074014 A1 Apr. 17, 2003

(51) Int. Cl.⁷ .............................................. A61B 17/32
(52) U.S. Cl. ....................... 606/170; 606/172
(58) Field of Search ................... 606/167, 172, 606/171, 170, 185

(56) References Cited

U.S. PATENT DOCUMENTS

| | | | | |
|---|---|---|---|---|
| 4,491,132 A | * | 1/1985 | Aikins | 128/305 |
| 4,499,898 A | * | 2/1985 | Knepshield et al. | 128/305 |
| 4,516,575 A | * | 5/1985 | Gerhard et al. | 128/305 |
| 4,534,348 A | * | 8/1985 | Fedorov et al. | 128/305 |
| 4,730,613 A | * | 3/1988 | Gordy | 128/305 |
| 5,569,282 A | | 10/1996 | Werner | 606/167 |
| 5,591,186 A | * | 1/1997 | Wurster et al. | 606/170 |
| 5,611,808 A | | 3/1997 | Hossain et al. | 606/170 |
| 5,618,294 A | | 4/1997 | Aust et al. | 606/170 |
| 5,620,415 A | | 4/1997 | Lucey et al. | 604/22 |
| 5,690,664 A | * | 11/1997 | Sauer et al. | 606/185 |
| 5,885,288 A | | 3/1999 | Aust et al. | 606/170 |
| 5,908,432 A | * | 6/1999 | Pan | 606/167 |
| 6,152,894 A | | 11/2000 | Kubler | 604/22 |
| 6,162,214 A | | 12/2000 | Mueller et al. | 606/15 |

OTHER PUBLICATIONS

Mueller "The Surgical Armamentarium" p. 3 (1980).*

* cited by examiner

Primary Examiner—Michael H. Thaler
(74) Attorney, Agent, or Firm—Gordon & Jacobson, P.C.

(57) ABSTRACT

A surgical knife device includes a tubular shaft, a blade guide at the distal end of the shaft, an actuation wire extending through the shaft, a blade coupled to the distal end of the wire, and a handle which moves the wire relative to the shaft to effect extension and retraction of the blade from the guide. The blade height is substantially the same as the outer diameter of the distal end of the shaft and the blade guide to provide a large cutting surface. Movement of the blade is effected with a knob rotatably coupled to the handle and which provides fine longitudinal movement of the blade. The device is also preferably steerable such that it may be controllably articulated about a flexible distal portion of the shaft.

10 Claims, 8 Drawing Sheets

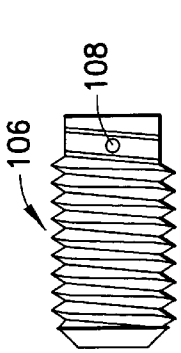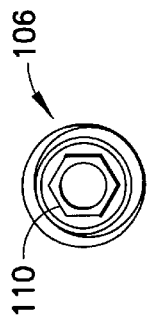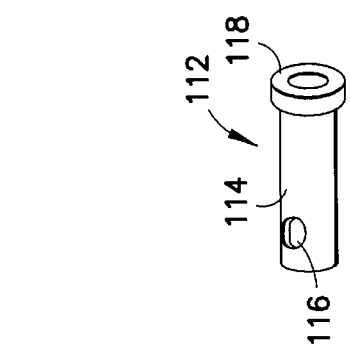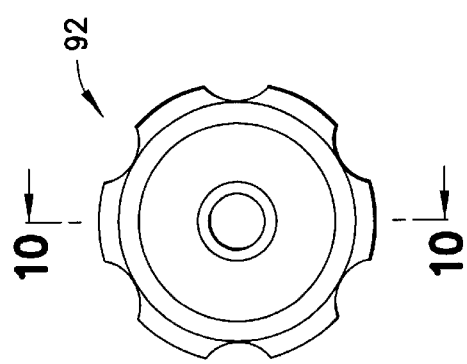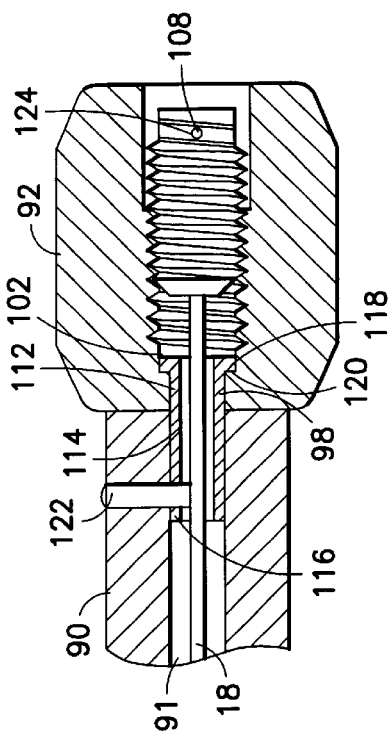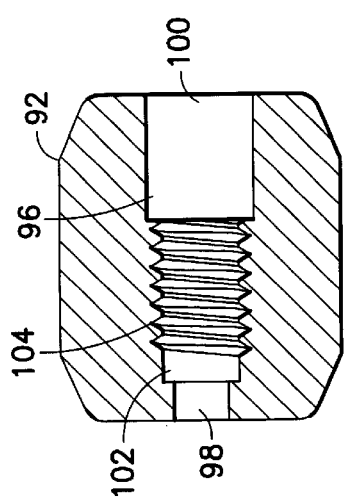

ARTICULABLE AND RECIPROCABLE SURGICAL KNIFE

BACKGROUND OF THE INVENTION

1. Field of the Invention

This invention relates broadly to surgical instruments. More particularly, this invention relates to probe-like cutting instruments for use in surgical procedures.

2. State of the Art

The development of minimally invasive surgical procedures, such as endoscopic and laparoscopic procedures, has created a great demand for devices well-adapted for use during such procedures. More particularly, when performing port access surgery, such as when endoscopically performing an arteriotomy, it is sometimes necessary to make very accurate incisions. Because of the limitations imposed by the entry site with respect to the location and orientation of the surgical site, it is desirable to be able to control the blade penetration depth as well as the approach angle of the blade toward the surgical site. The latter allows the surgeon to make an incision in the plane that is most desirable. Generally, this angle would be perpendicular to the surface being incised.

SUMMARY OF THE INVENTION

It is therefore an object of the invention to provide an endoscopic surgical knife in which the depth of the blade exposure can be finely controlled while the device is in use.

It is another object of the invention to provide an endoscopic surgical knife in which the angle of the blade can be controlled while the device is in use.

It is a further object of the invention to provide an endoscopic surgical knife which remains stable at a desired angle.

It is an additional object of the invention to provide an endoscopic surgical knife in which the blade is completely retractable so that it does not become damaged or cause damage upon introduction through or withdrawal from a port.

It is also an object of the invention to provide an endoscopic surgical knife having a relatively small shaft.

It is still another object of the invention to provide an endoscopic surgical knife which maximizes the blade size relative to the shaft.

In accord with these objects, which will be discussed in detail below, a surgical knife device is provided which includes a tubular shaft, a blade guide at the distal end of the shaft, a blade depth control member extending through the shaft, and a blade coupled to the distal end of the blade depth control member. A proximal handle moves the blade depth control wire relative to the shaft such that the blade moves relative to the blade guide. According to a preferred aspect of the invention, the blade height is substantially the same as the outer diameter of the distal end of the shaft and the blade guide. As such, the blade has a relatively large cutting surface. The blade is moved between a retracted position in which the blade is positioned substantially completely within the blade guide and an extended position in which at least a portion of the blade extends distally from the blade guide.

According to another preferred aspect of the invention, movement of the blade between retracted and extended positions is effected with a knob rotatably coupled to the handle. The knob includes an axial threaded bore, and the proximal end of the blade depth control member is provided with a threaded adapter which at least partially resides in the bore of the knob. When the knob is rotated, the adapter is longitudinally moved within the bore and the blade depth control member coupled to the blade is likewise longitudinally moved to effect movement of the blade. Using the knob, fine and controllable longitudinal movement of the blade is enabled.

According to a further preferred aspect of the invention, steering members extend from the handle through the shaft on either side of the blade depth control member and are coupled to adjacent a flexible distal portion of the shaft. The handle is provided with a means, e.g., a steering knob, for moving one steering member relative to the other to cause the shaft to bend about a flexible distal portion such that the device is articulable.

Additional objects and advantages of the invention will become apparent to those skilled in the art upon reference to the detailed description taken in conjunction with the provided figures.

BRIEF DESCRIPTION OF THE DRAWINGS

FIG. 9 is an end view of an actuation knob according to the invention;

FIG. 10 is a section view across line 10—10 in FIG. 9;

FIG. 11 is a perspective view of a knob retainer according to the invention;

FIG. 12 is a side elevation of a threaded adapter according to the invention;

FIG. 13 is an end view of the threaded adapter of FIG. 12;

FIG. 14 is a partial section broken elevation view of the assembly of the actuation knob to the shank of the handle and the actuation mechanism for moving the blade actuation control wire;

DETAILED DESCRIPTION OF THE PREFERRED EMBODIMENTS

Figure 1:
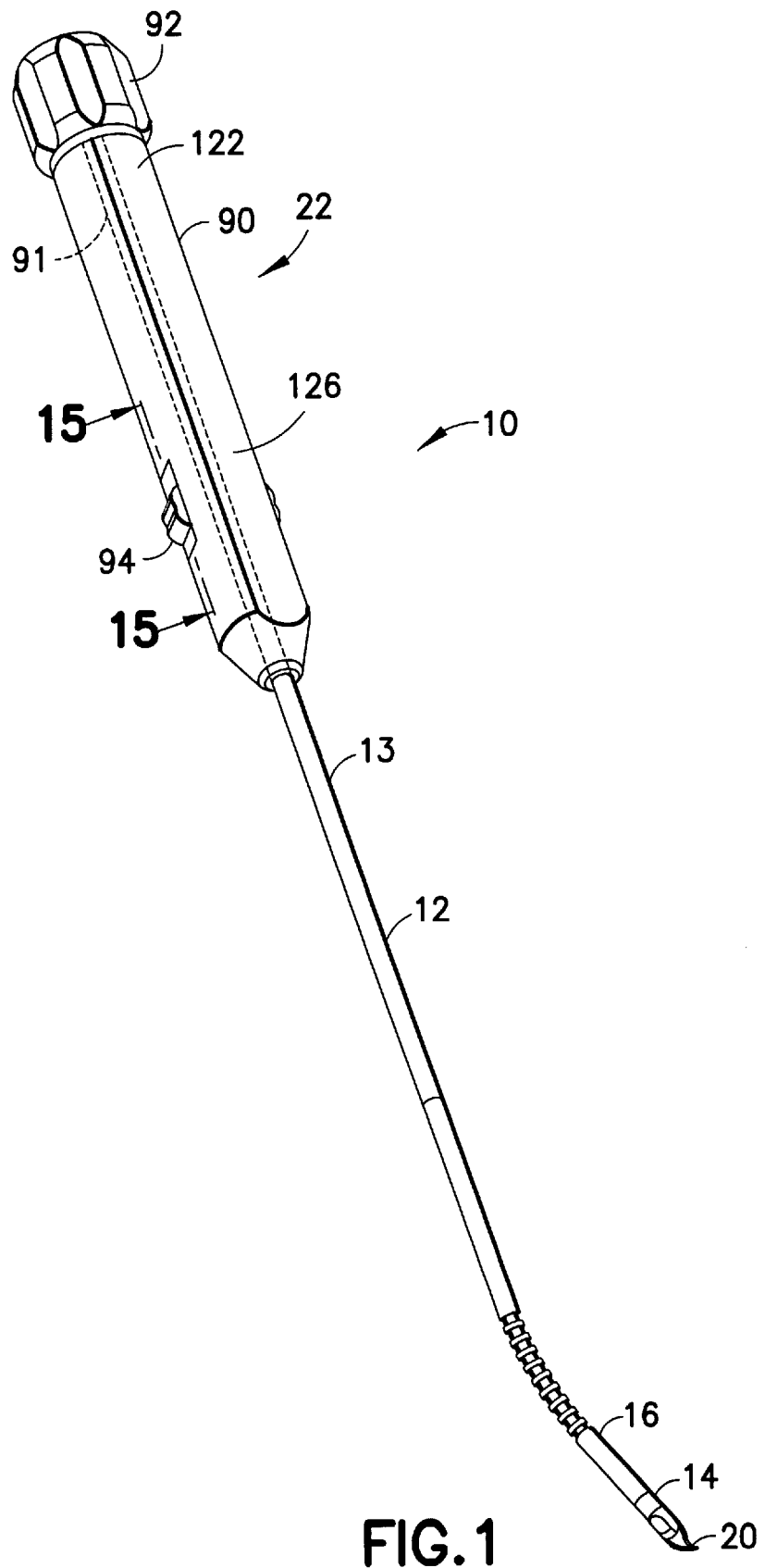
FIG. 1 perspective view of a first embodiment of an articulable and reciprocable surgical knife according to the invention.
Figure 2:
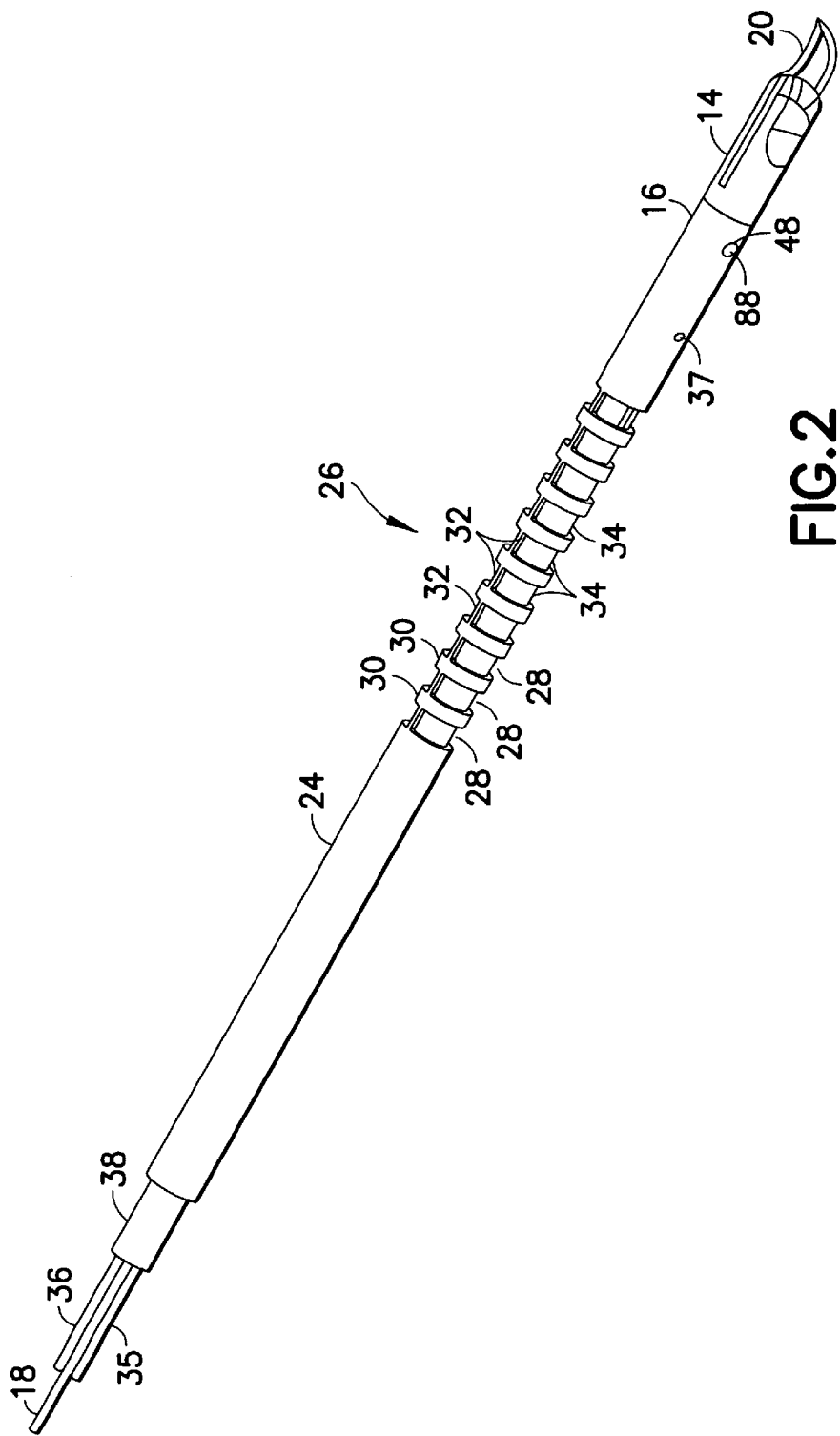
FIG. 2 is a broken perspective view of a distal end of the first embodiment of the surgical knife according to the invention.

Turning now to FIGS. 1 and 2, a surgical knife device 10 includes a tubular shaft, a blade guide 14 coupled to the distal end 16 of the shaft 12, a blade depth control wire 18 extending through the shaft 12, and a blade 20 coupled to the distal end of the blade depth control member 18. A proximal handle 22 is adapted to move the blade depth control member 18 relative to the shaft 12 such that the blade 20 moves relative to the blade guide 14, as described in detail below, between retracted and extended positions.

The shaft 12 includes a proximal rigid portion 13. The rigid portion 13 facilitates through-port use of the device in that the rigid portion may be gripped or clamped by another device to stably hold the device 10. Referring particularly to FIG. 2, a distal section 24 of the shaft 12 is provided with a flexible portion 26. The flexible portion 26 preferably includes a plurality of opposing slots 28 defining rings 30 and upper and lower struts 32, 34 which permit the flexible portion to laterally bend about the struts. The shaft preferably has a diameter of approximately 5 to 6 mm. The shaft 12 is preferably made from stainless steel or nickel-titanium alloy.

Two steering control wires 35, 36 extend from the handle 22 through the tubular shaft 12, one on either side of the blade depth control wire 18, and are coupled at their distal ends to attachment holes 37 (only one shown) in the shaft distal of the flexible portion 26. Movement of one wire relative to the other, as described below, causes the shaft 12 to flex at the flexible portion 26, and thereby provides directability to the device. A flexible tubular wire guide (sheath) 38 is preferably provided around at least a distal portion of the blade depth control wire 18 and the steering control wires 35, 36 and substantially prevents human tissue from entering the slots 28 and inhibiting functioning of the device.

Figure 3:
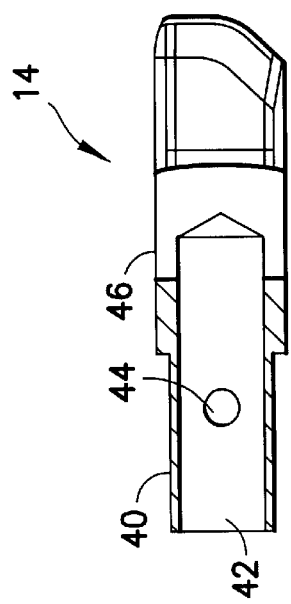
FIG. 3 is a partial side elevation of a blade guide according to the invention.
Figure 4:
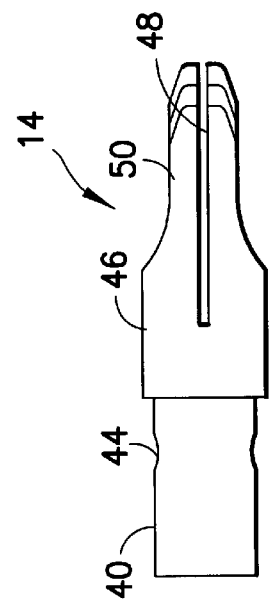
FIG. 4 is a top view of the blade guide of FIG. 3.

Referring to FIGS. 2 through 4, the blade guide 14 includes a proximal portion 40 having a rear bore 42 and a lateral cross pin hole 44, and a distal portion 46. The outer diameter of the blade guide 14 is stepped between the proximal and distal portions, with the proximal portion 40 being smaller than the distal portion 46 and sized to be received within the distal end 16 of the shaft 12 such that a relatively constant diameter is provided from the shaft 12 to the distal portion 46 of the blade guide. Referring to FIGS. 2 through 4, the distal end 16 of the shaft 12 is also provided with a cross pin hole 48 which is aligned with the cross pin hole 44 of the guide 14. The distal portion 46 of the blade guide 14 includes a blade slot 50, and a laterally tapering profile which provides clearance for endoscopic viewing of the blade.

Figure 5:
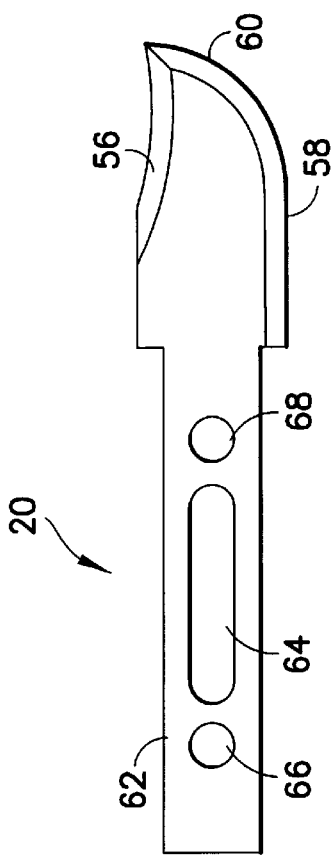
FIG. 5 is a side elevation of a surgical knife blade according to the invention.
Figure 6:
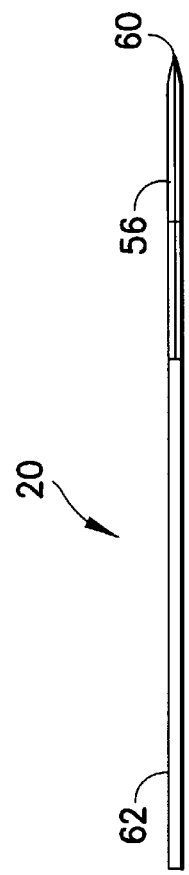
FIG. 6 is a top view of the blade of FIG. 5.
Figure 7:
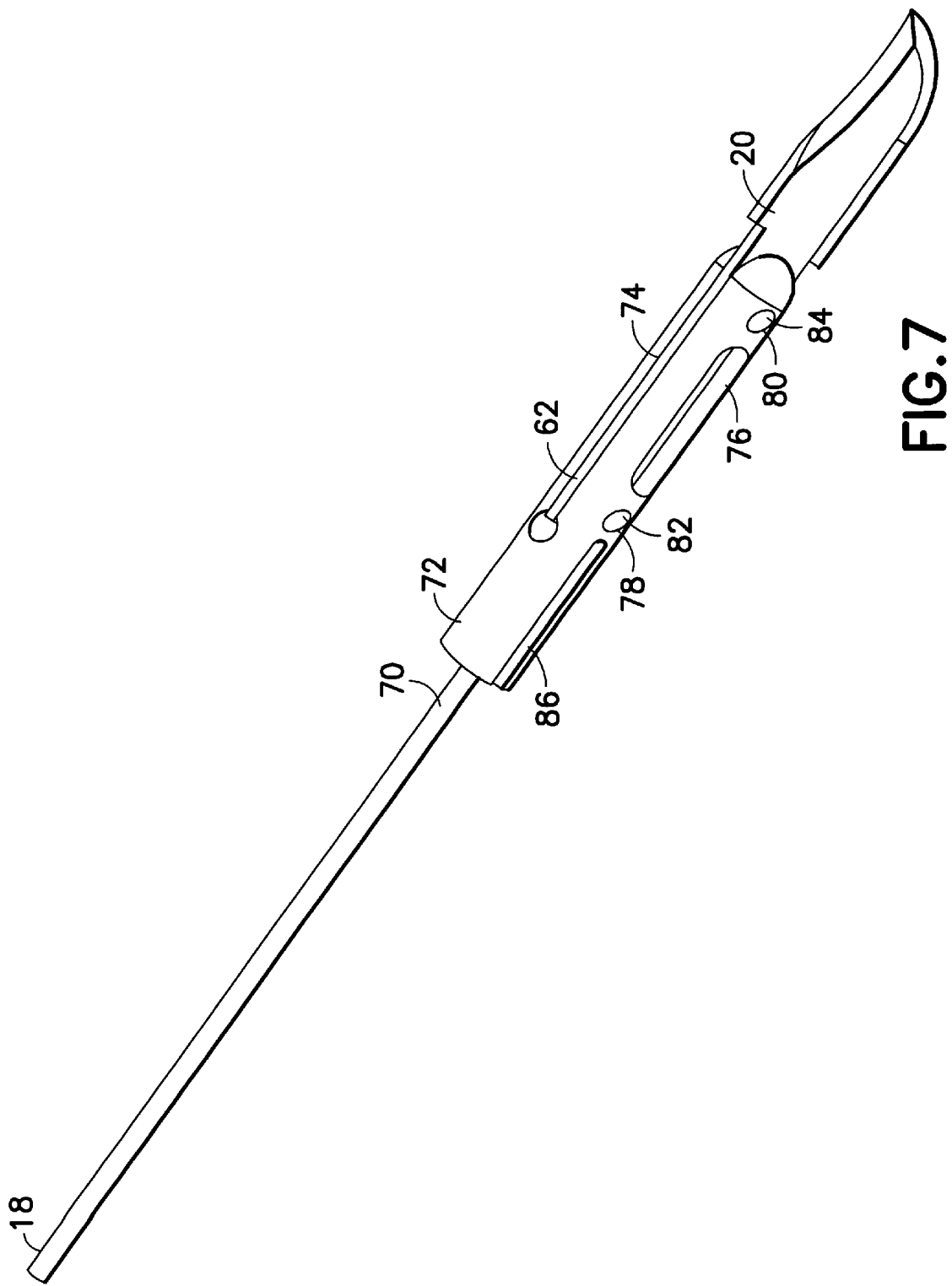
FIG. 7 is a broken perspective view of the blade, a blade holder, and a distal end of a blade depth control wire according to the invention.

Referring to FIGS. 5 and 6, the blade 20 has upper, lower, and distal cutting surfaces 56, 58, 60 respectively, with the lower and distal surfaces 58, 60 preferably defining a continuous curving surface. The blade 20 also includes a proximal tang 62 provided with a longitudinal slot 64, and coupling holes 66, 68. The cutting portion of the blade (comprising the cutting surfaces 56, 58, and 60) preferably extends 0.28 inches, while the tang 62 preferably has a length of approximately 0.47 inches. The blade has a maximum height of approximately 0.13–0.14 inches, and the distal surface preferably has a radius of curvature of approximately 0.134 inches. Referring to FIG. 7, the blade 20 is coupled to the distal end 70 of the blade depth control wire 18 with a blade coupler 72. The blade coupler 72 includes a rear bore which receives and holds the distal end 70 of the blade depth control wire 18, a distal tang slot 74 into which the blade tang 62 is received, and a longitudinal slot 76 and coupling holes 78, 80 in alignment with the slot 64 and holes 66, 68 of the blade tang 62. Cross pins 82, 84 are secured within holes 66 and 78, and holes 68 and 80 to secure the blade 20 to the coupler 72. In addition, the proximal end of the coupler includes two clearance slots 86, one on each side, each adapted to receive one of the steering wires 35, 36 and guide the steering wires to attachment holes 37 (FIG. 2).

Figure 8:
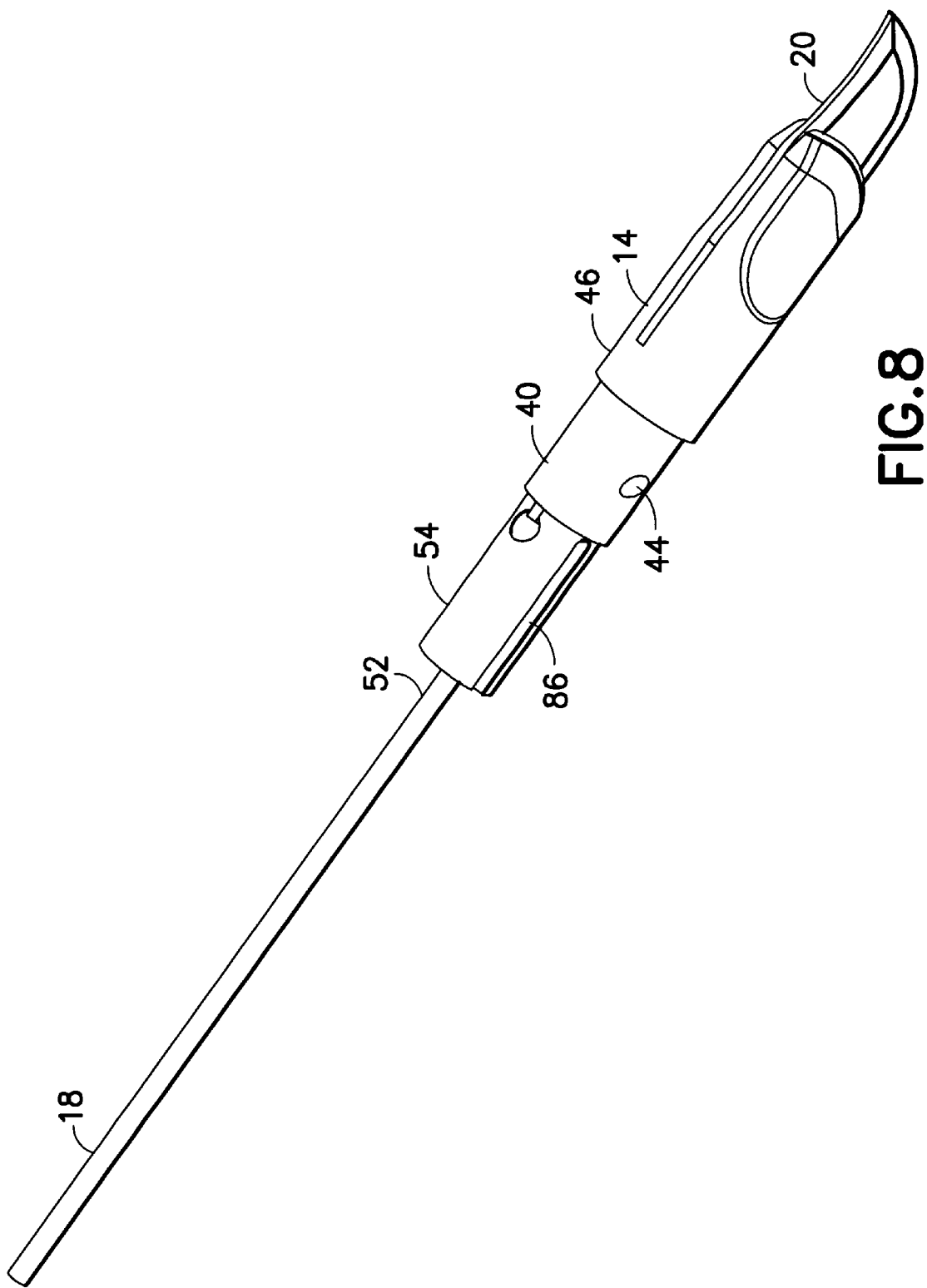
FIG. 8 is a broken perspective view of the blade and a blade holder assembled with the blade guide according to the invention.

Referring to FIGS. 2 and 8, the blade guide is then positioned over portions of the assembled blade 20 and coupler 54, and the distal end 16 of the shaft 12 is positioned over the proximal end of the blade guide. A cross pin 88 is inserted into cross pin holes 44 and 48 and through the longitudinal slots 64, 76. As such, cross pin 88 secures the shaft 12 to the guide 14 and also limits longitudinal movement of the blade 20 relative to the cross pin 88. According to a preferred aspect of the invention, the height of the blade is substantially the same as the outer diameter of the distal portion 46 of blade guide 14 and the distal end 16 of the shaft 12. As such, the blade 20 has a large maximum exposure for cutting.

Turning back to FIG. 1, according to the first embodiment of the invention, the handle 22 includes a stationary portion (shank) 90 having a longitudinal bore 91, an actuation knob 92, and a steering knob 94. Referring to FIGS. 9 and 10, the actuation knob 92 includes a stepped axial bore 96 having three portions each with a different diameter: a distal portion 98 having the smallest diameter, a proximal portion 100 having the largest diameter, and a central portion 102. The central portion 102 includes threads 104. Referring to FIG. 11, the actuation knob 92 is coupled to the shank 90 with a knob retainer 112. The knob retainer 112 includes a hollow tubular portion 114 having a radial hole 116 and an enlarged lip 118. Referring to FIG. 14, the retainer 112 is fed into the actuation knob 92 from the proximal side such that the tubular portion 114 extends into the proximal end of the bore 91 of the shank 90 and the lip 118 rests against the step 120 formed at the intersection of the distal and central portions 98, 102. A pin 122 extends radially into the shank 90 and into the radial hole 116 to fixedly secure the retainer, and rotatably mount the actuation knob 92 to the shank 90 such that it has an axis of rotation parallel to, and preferably coaxial with, the axis of the shank.

Referring to FIGS. 12 through 14, the proximal end 124 (FIG. 14) of the blade depth control wire 18 extends into a threaded adapter 106 and is coupled thereto at an attachment hole 108. The adapter 106 is threaded into the central portion 102 of the bore 96 from the distal portion 100 of the bore 96. The threaded adapter 106 include a rear hex opening 110 which can receive a tool to facilitate the threaded engagement during assembly.

Referring to FIGS. 1 and 9 through 14, rotation of the actuation knob 92 causes the threaded adapter 106 to move longitudinally relative to the threaded central portion 102. This results in movement of the blade 20 relative to the blade guide, i.e., extension and retraction of the blade in the guide 14, without rotating the blade 20 relative to the shaft 12. Using the actuation knob 92, fine and controllable longitudinal movement of the blade 20 is enabled.

Figure 15:
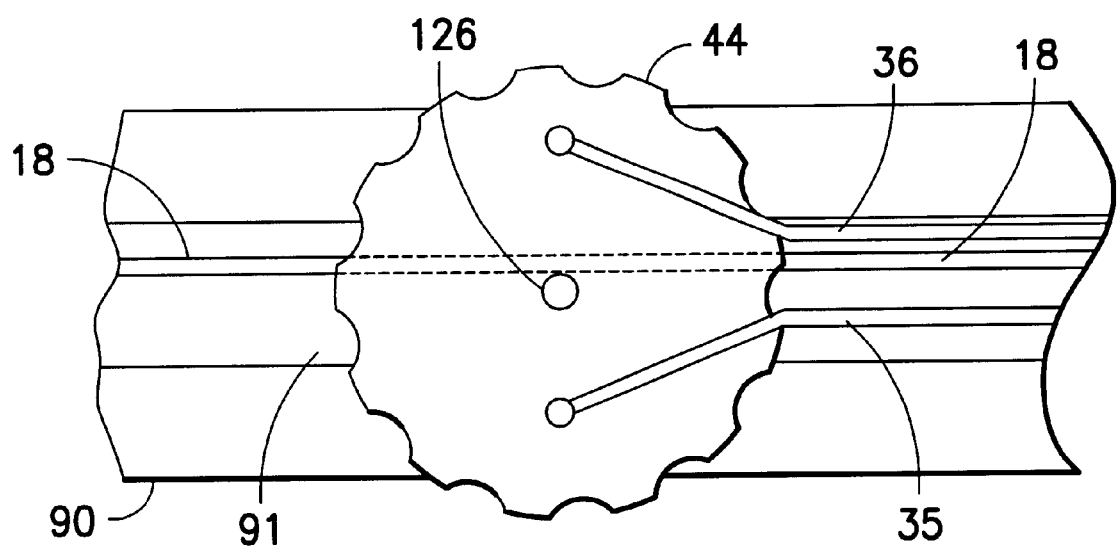
FIG. 15 is a broken section view across line 15—15 in FIG. 1 of the steering knob assembly.

Referring to FIG. 15, the steering knob 94 extends through and is rotatably mounted partially within the shank 90 on a pin 126, with an axis of rotation preferably perpendicular to both the shank 90 and a plane defined by the extension of the parallel steering wires 35, 36. A proximal end of each of the steering wires 35, 36 extends through the distal portion of the bore 91 in the shank and is coupled to the steering knob 94. When the steering knob 94 is rotated on the pin 126, one steering wire, e.g. 36, is pulled proximally relative to the other, e.g. 35, to cause the flexible portion 26 to flex in the direction of the pulled wire 36, as shown in FIG. 1.

Figure 16:
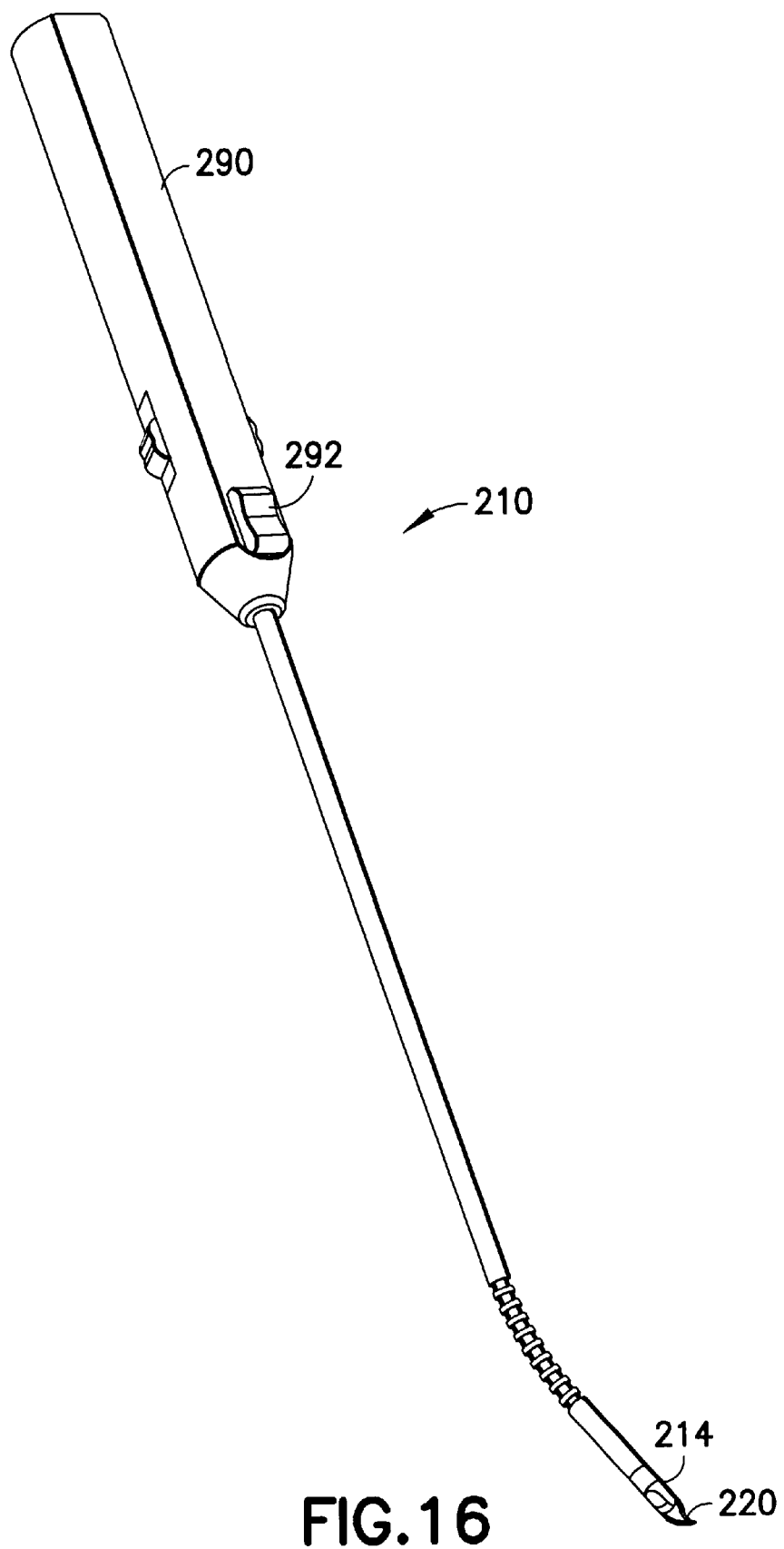
FIG. 16 is a perspective view of a second embodiment of a surgical knife device according to the invention.

Turning now to FIG. 16, according to a second embodiment of the surgical knife device 210 of the invention, substantially similar to the first embodiment, the movement of the blade 220 is controlled by a control button 292 which is coupled to the proximal end of a blade depth control wire (not shown) and slidably mounted on the shank 290 for longitudinally movement relative thereto to effect extension and retraction of the blade relative to the blade guide 214.

There have been described and illustrated herein embodiments of a surgical knife device. While particular embodiments of the invention have been described, it is not intended that the invention be limited thereto, as it is intended that the invention be as broad in scope as the art will allow and that the specification be read likewise. Thus, while the device preferably has a steerable distal end, it will be appreciated that the surgical knife can be provided without steerability; i.e., without the steering wires and steering knob, and even with a shaft which is substantially rigid along its length. In addition, while control wires are described for actuation and steering of the blade, it will be appreciated that other flexible control members, e.g., cables, ribbons, non-metal filaments, etc., can also be used. Moreover, in a non-steerable embodiment, a rigid blade depth control member can be used. Also, while the shaft is preferably made from a metal or metal alloy, it will be appreciated that a suitable axially rigid plastic or an axially reinforced more flexible plastic may be used. Furthermore, while the construction of a particularly preferred flexible portion is described, it will be appreciated that other structure, or even different materials from the proximal portion, can be provided to make the distal portion of the device flexible for steering. Also, while cylindrical or disk-like actuation and steering knobs are disclosed, it will be appreciated that actuation and steering members of other shapes can be used; e.g., elongate levers, hexagonal members, etc. Moreover, while the actuation knob is shown at the proximal end of the shank, it will be appreciated that it may be located at the distal end of the shank. In addition, while the blade guide is a preferred element of the invention, it is not a necessary part of the invention, and the blade can alternatively be retracted into a slit distal end of the shaft when a blade guide is not provided. It will therefore be appreciated by those skilled in the art that yet other modifications could be made to the provided invention without deviating from its spirit and scope as claimed.

What is claimed is:

1. A surgical knife device, comprising:
   a) an elongate tubular shaft having proximal and distal ends and an outer diameter;
   b) a handle coupled to said proximal end of said shaft and having a longitudinal bore therein;
   c) a blade in a first orientation said blade having a height substantially equal to the outer diameter;
   d) a flexible blade depth control member having proximal and distal ends, said proximal end extending into said longitudinal bore of said handle and said distal end extending to or adjacent said distal end of the shaft and coupled to said blade; and
   e) an actuation member rotatably coupled to said handle and coupled to said proximal end of said blade depth control member, wherein rotation of said actuation member relative to said handle moves said blade longitudinally relative to said distal end of said shaft.

2. A surgical knife device according to claim 1, wherein: said blade remains in said first orientation when said actuation member is rotated relative to said handle.

3. A surgical knife device according to claim 1, wherein: said actuation member is a knob.

4. A surgical knife device according to claim 1, wherein: said shaft includes a substantially rigid proximal portion and a flexible distal portion.

5. A surgical knife device according to claim 4, further comprising:
   f) means for articulating said shaft about said flexible distal portion.

6. A surgical knife device according to claim 1, further comprising:
   f) a blade coupler,
      wherein said blade includes a tang portion, said tang portion and said distal end of said blade depth control member being coupled to said blade coupler.

7. A surgical knife device, comprising:
   a) an elongate tubular shaft having proximal and distal ends;
   b) a handle coupled to said proximal end of said shaft and having a longitudinal bore therein;
   c) a blade in a first orientation;
   d) a flexible blade depth control member having proximal and distal ends, said proximal end extending into said longitudinal bore of said handle and said distal end extending to or adjacent said distal end of the shaft and coupled to said blade;
   e) an actuation member rotatably coupled to said handle and coupled to said proximal end of said blade depth control member, wherein rotation of said actuation member relative to said handle moves said blade longitudinally relative to said distal end of said shaft; and
   f) a threaded adapter coupled to said proximal end of said blade depth control member,
      wherein said actuation member includes a threaded bore in which said threaded adapter is at least partially provided, such that rotation of said actuation member causes said adapter to move longitudinally through said threaded bore.

8. A surgical knife device, comprising:
   a) an elongate tubular shaft having proximal and distal ends;
   b) a handle coupled to said proximal end of said shaft and having a longitudinal bore therein;
   c) a blade in a first orientation;
   d) a flexible blade depth control member having proximal and distal ends, said proximal end extending into said longitudinal bore of said handle and said distal end extending to or adjacent said distal end of the shaft and coupled to said blade;
   e) an actuation member rotatably coupled to said handle and coupled to said proximal end of said blade depth control member, wherein rotation of said actuation member relative to said handle moves said blade longitudinally relative to said distal end of said shaft; and
   f) a blade guide at said distal end of said shaft, said blade guide having a maximum outer diameter, and said blade having a height substantially equal to said maximum outer diameter,
      wherein when said blade is moved distally relative to said distal end of said shaft, said blade is extended from said blade guide, and when said blade is moved proximally relative to said distal end of said shaft, said blade is retracted into said blade guide.

9. A surgical knife device, comprising:
a) an elongate tubular shaft having proximal and distal ends, an outer diameter, and a flexible portion;
b) a blade having a height substantially equal to said outer diameter of said shaft;
c) a handle coupled to said proximal end of said shaft and having a longitudinal bore therein;
d) an actuation member having proximal and distal ends, said proximal end extending into said longitudinal bore of said handle and said distal end extending to or adjacent said distal end of said shaft and coupled to said blade;
e) means for moving said blade longitudinally relative to said distal end of said shaft;
f) means for articulating said shaft about said flexible portion.

10. A surgical knife device, comprising:
a) an elongate tubular shaft having proximal and distal ends and a flexible portion;
b) a blade guide coupled to said distal end of said shaft and having outer walls defining a maximum outer diameter;
c) a blade having a cutting edge and a height substantially equal to said maximum outer diameter of said blade guide;
d) a handle coupled to said proximal end of said shaft and having a longitudinal bore therein;
e) a blade depth control member having proximal and distal ends, said proximal end extending through said longitudinal bore of said handle and said distal end extending to or adjacent said distal end of the shaft and coupled to said blade;
f) means for moving said blade between retracted and extended position relative to said blade guide, wherein when in said retracted position said cutting edge of said blade is withdrawn between said walls of said blade guide; and
g) means for articulating said shaft about said flexible portion.

* * * * *